Figure 1A:
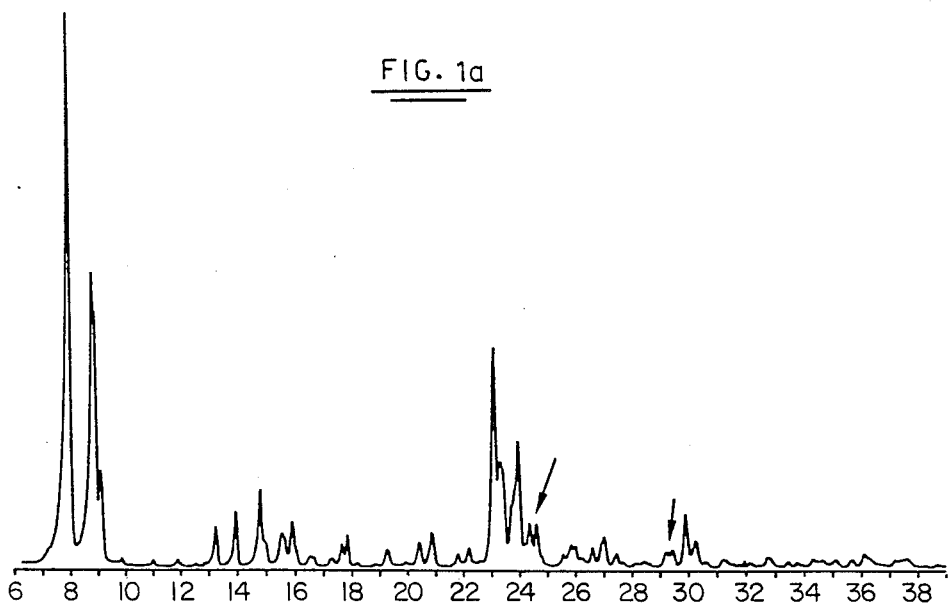

United States Patent [19]

Neri et al.

[11] Patent Number: 4,833,260

[45] Date of Patent: May 23, 1989

[54] PROCESS FOR THE EPOXIDATION OF OLEFINIC COMPOUNDS

[75] Inventors: Carlo Neri, S. Donato Milanese; Bartolomeo Anfossi, Milan; Antonio Esposito; Franco Buonomo, both of S. Donato Milanese, all of Italy

[73] Assignee: Anic S.p.A., Palermo, Italy

[21] Appl. No.: 142,538

[22] Filed: Jan. 11, 1988

Related U.S. Application Data

[63] Continuation of Ser. No. 772,922, Sep. 5, 1986, abandoned, which is a continuation of Ser. No. 513,807, Jul. 14, 1983, abandoned.

[30] Foreign Application Priority Data

Jul. 28, 1982 [IT] Italy .................. 22608 A/82

[51] Int. Cl.$^4$ .......................................... C07D 301/12
[52] U.S. Cl. ................................................. 549/531
[58] Field of Search .......................................... 549/531

[56] References Cited

U.S. PATENT DOCUMENTS 3,156,709 11/1964 Allan ................................... 549/531
3,351,635 11/1967 Kollar ................................. 549/529
3,641,066 2/1972 Rouchand et al. .................. 549/533
4,021,454 5/1977 Wulff et al. ......................... 549/529
4,026,908 5/1977 Pralus et al. ........................ 549/531
4,410,715 10/1983 McMullen et al. ................. 549/531

Primary Examiner—Richard L. Raymond
Assistant Examiner—Mark W. Russell
Attorney, Agent, or Firm—Hedman, Gibson, Costigan & Hoare

[57] ABSTRACT

A process for the epoxidation of olefinic compounds, consisting of reacting said compounds with hydrogen peroxide either introduced as such or produced by substances capable of generating it under the reaction conditions, in the presence of synthetic zeolites containing titanium atoms, of general formula:

$$xTiO_2 \cdot (1-x)SiO_2,$$

where x lies between 0.0001 and 0.04, and possibly in the presence of one or more solvents, operating at a temperature of between 0° and 150° C., and at a pressure of between 1 and 100 ata.

12 Claims, 2 Drawing Sheets

PROCESS FOR THE EPOXIDATION OF OLEFINIC COMPOUNDS

This is a continuation of U.S. Application Ser. No. 722,922 filed Sept. 5, 1986, now abandoned, which is a continuation of U.S. Application Ser. No. 513,807 filed July 14, 1983, now abandoned.

This invention relates to a process for the epoxidation of olefinic compounds by means of hydrogen peroxide either introduced as such or produced by substances capable of generating it under the reaction conditions, in the presence of synthetic zeolites containing titanium atoms.

Hydrogen peroxide when in the presence of suitable derivatives of transition metals (mo, V, W, Ti etc.) is known to be able to attack olefinic double bonds, with the formation of epoxides and/or glycols. The glycol quantity present is a function of the quantity of water introduced with the hydrogen peroxide, and consequently in order to obtain high epoxide selectivity it is necessary to use very concentrated hydrogen peroxide ($\geq 70\%$), with obvious safety problems due to the violent decomposition of the hydrogen peroxide, or to use solvent mixtures able to azeotropically remove the water accompanying the $H_2O_2$ and the water of reaction.

It is likewise known that polar solvents (of which water is one) kinetically retard the epoxidation reaction.

We have surprisingly found that a synthetic zeolite containing titanium atoms is able to selectively epoxidise the olefins with high epoxide yields even though working with hydrogen peroxide in aqueous solution, and even when diluted to a low concentration such as 10% (the usual being 10-70%).

The subject matter of the present invention is a process for the epoxidation of olefinic compounds consisting of reacting said compounds with hydrogen peroxide either introduced as such or produced by substances capable of generating it under the reaction conditions, in the presence of synthetic zeolites containing titanium atoms (titanium silicalites), of the following general formula:

$$xTiO_2.(1-x)SiO_2,$$

where x lies between 0.0001 and 0.04, and possibly in the presence of one or more solvents.

The synthetic zeolites used for the epoxidation reaction are described in Belgian Pat. No. 886,812, of which we repeat some points illustrating the material and relative method of preparation.

The composition range of the titanium silicalite expressed in terms of molar ratios of the reagents is as follows:

| Molar ratio of reagents | | preferably |
|---|---|---|
| $SiO_2/TiO_2$ | 5-200 | 35-65 |
| $OH^-/SiO_2$ | 0.1-1.0 | 0.3-0.6 |
| $H_2O/SiO_2$ | 20-200 | 60-100 |
| $Me/SiO_2$ | 0.0-0.5 | 0 |
| $RN^+/SiO_2$ | 0.1-2.0 | 0.4-1.0 |

$RN^+$ indicates the nitrogenated organic cation deriving from the organic base used for the preparation of the titanium silicalite (TS-1).

Me is an alkaline ion, preferably Na or K.

The final US-1 has a composition satisfying the formula $xTiO_2.(1-x)SiO_2$, where x lies between 0.0001 and 0.04, and preferably between 0.01 and 0.025. The TS-1 is of the silicalite type, and all the titanium substitutes the silicon.

The synthetic material has characteristics which are shown up by X-ray and infrared examination.

Figure 1B:
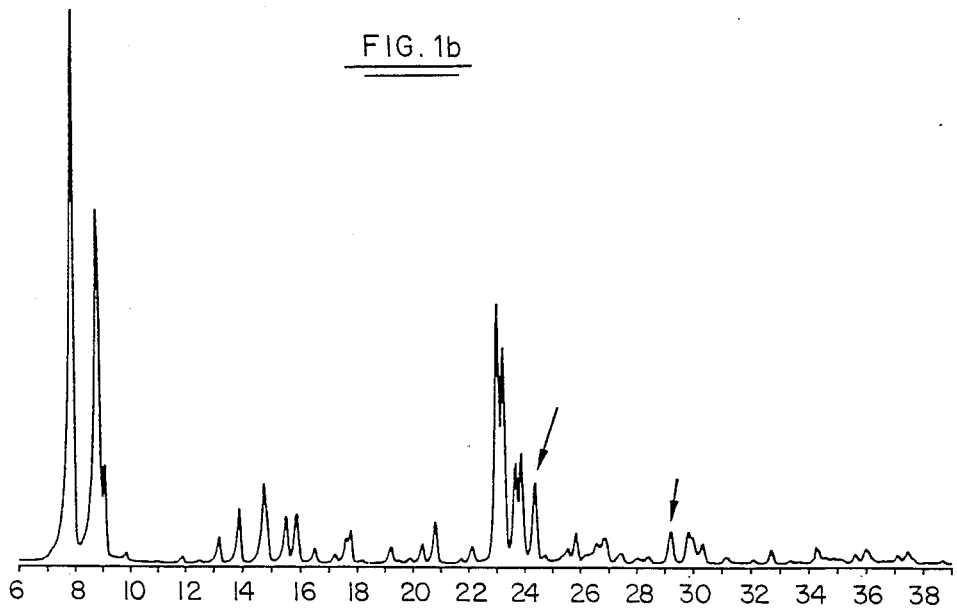

The X-ray examination is carried out by means of a powder diffractometer provided with an electronic pulse counting system, using the radiation CuKd$^-$. The titanium silicalites (TS-1) are characterised by a X-ray diffraction spectrum as shown in FIG. 1b. This spectrum is similar overall to the typical spectrum of silicalite (FIG. 1a), however it has certain clearly "single" reflections where double reflections are evident in the pure silicalite spectrum.

Because the spectral differences between TS-1 and silicalite are relatively small, special accuracy is required in the spectral determination. For this reason TS-1 and silicalite were examined by the same apparatus, using $Al_2O_3$ as the internal standard.

Table 1 shows the most significant spectral data of a TS-1 where x=0.017, and of a pure silicalite.

The constants of the elementary crystalline cell were determined by the minimum square method, on the basis of the interplanar distances of 7-8 single reflections lying within the range of $10°-40°$ $2\theta$.

A large proportion of the interplanar distances of TS-1 are tendentially greater than the corresponding distances of pure silicalite, although only slightly, which is in accordance with the larger predictable value of the Ti—O bond distance relative to that of the Si—O bond distance.

Passage from a double reflection to a single reflection is interpreted as a change from a monoclinic symmetry (pseudo orthorhombic) (silicalite) to an effective orthorhombic symmetry, "titanium silicalite" (TS-1). In FIG. 1, the most apparent aforesaid spectral differences are indicated by arrows.

INFRARED EXAMINATION. TS-1 shows a characteristic absorption band at about 950 cm$^{-1}$ (see FIG. 2, spectra B, C and D) which is not present in the pure silicalite spectrum (FIG. 2, spectrum A), and is also absent in titanium oxides (rutile, anastase) and in alkaline titanates.

Spectrum B is that of TS-1 with 5 mol% of $Ti_2$, spectrum C is that of TS-1 with 8 mol% of $TiO_2$, and spectrum D is that of TS-1 with 2.3 mol% of $TiO_2$.

Figure 2:
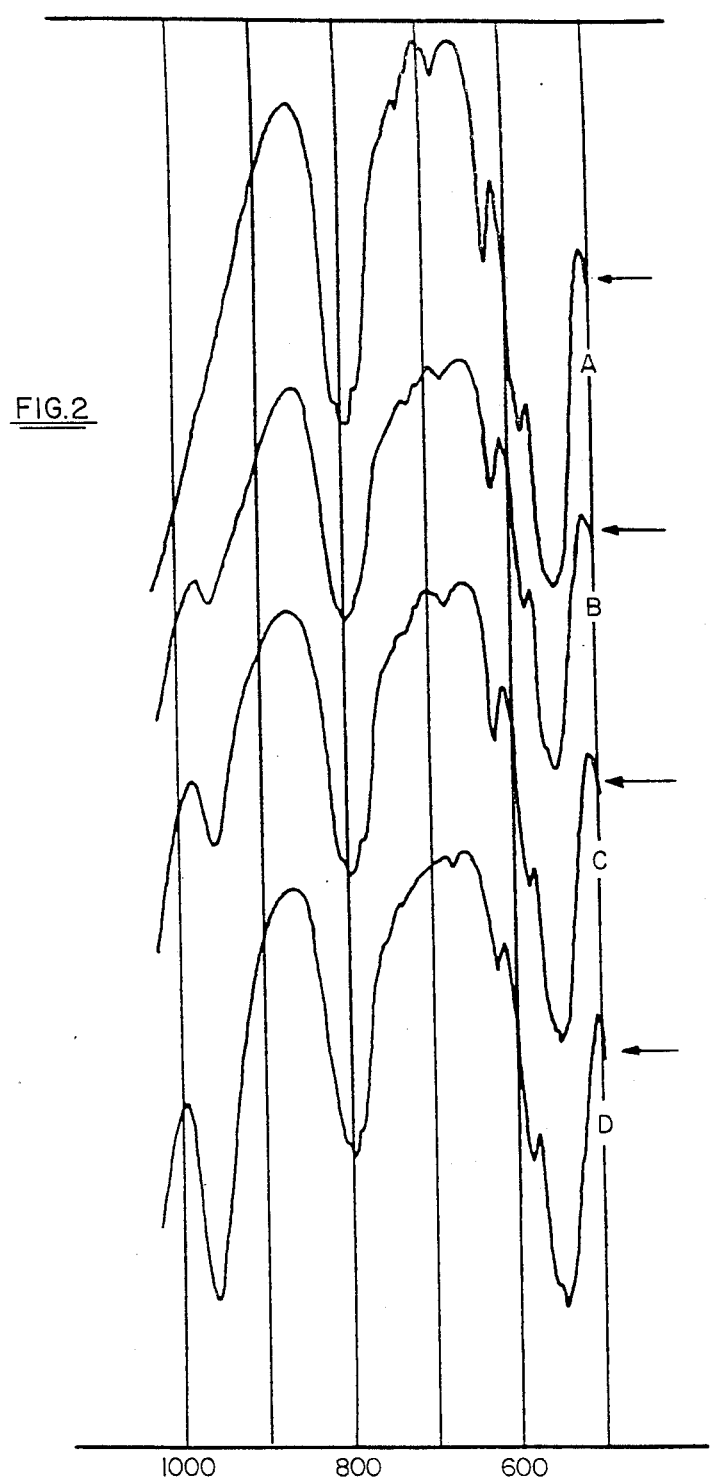

As can be seen from FIG. 2, the band intensity at approximately 950 cm$^{-1}$ increases with the quantity of titanium which substitutes the silicon in the silicalite structure.

MORPHOLOGY. From a morphological aspect, TS-1 is in the form of parallelepipeds with chamfered edges. A X-ray microprobe examination has shown that the titanium distribution within the crystal is perfectly uniform, thus confirming that the titanium substitutes the silicon in the silicalite structure, and is not present in other forms.

The process for preparing titanium silicalite comprises the preparation of a reaction mixture consisting of sources of silicon oxide, titanium oxide and possibly an alkaline oxide, a nitrogenated organic base and water, the composition in terms of the molar reagent ratios being as heretofore defined.

The silicon oxide source can be a tretraalkylorthosilicate, preferably tetraethylorthosilicate, or simply a silicate in colloidal form, or again a silicate of an alkaline metal, preferably Na or K.

The titanium oxide source is a hydrolysable titanium compound preferably chosen from $TiCl_4$, $TiOCl_2$ and $Ti(alkoxy)_4$, preferably $Ti(OC_2H_5)_4$.

The organic base is tetraalkylammonium hydroxide, and in particular tetrapropylammonium hydroxide.

The reagent mixture is subjected to hydrothermal treatment in an autoclave at a temperature of between 130° and 200° C. under its own developed pressure, for a time of 6–30 days until the crystals of the TS-1 precursor are formed. These are separated from the mother solution, carefully washed with water and dried. When in the anhydrous state they have the following composition: $XTiO_2.(1-x)SiO_2.0.04(RN^+)_2O$.

The precursor crystals are heated for between 1 and 72 hours in air at 550° C. to completely eliminate the nitrogenated organic base. The final TS-1 has the following composition: $xTiO_2.(1-x)SiO_2$, where x is as heretofore defined.

Chemical and physical examinations are carried out on the products thus obtained.

The epoxidation reaction between olefin and hydrogen peroxide is conducted at a temperature of between 0° and 150° C., at a pressure of between 1 and 100 ata.

Moreover, the epoxidation reaction can be carried out in batch or in a fixed bed, in a monophase or biphase system.

The catalyst is stable under the reaction conditions, and can be totally recovered and reused.

The solvents which can be used include all polar compounds such as alcohols, ketones, ethers, glycols and acids, with a number of carbon atoms which is not too high and is preferably less than or equal to 6.

Methanol or tert.butanol is the most preferred of the alcohols, acetone the most preferred of the ketones, and acetic or propionic acid the most preferred of the acids.

The olefinic compounds which can be epoxidated according to the invention are of general formula

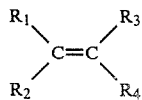

where $R_1$, $R_2$, $R_3$ and $R_4$, which can be the same or different, can be H, or an alkyl, alkylaryl, cycloalkyl or alkylcycloalkyl radical, the alkyl radical having between 1 and 20 carbon atoms, the alkylaryl radical having between 7 and 20 carbon atoms, the cycloalkyl radical having between 6 and 10 carbon atoms, and the alkylcycloalkyl radical having between 7 and 20 carbon atoms.

The radicals $R_1$, $R_2$, $R_3$ and $R_4$ can constitute saturated or unsaturated rings in pairs.

Finally, the radicals $R_1$, $R_2$, $4R_3$ and $R_4$ can contain halogen atoms, preferably Cl, Br or I, and nitro, sulphonic, carbonyl, hydroxyl, carboxyl and ether groups.

By way of example, the olefins which can be epoxidated by this process are ethylene, propylene, allyl chloride, butene-2, 1-octene, 1-tridecene, mesityl oxide, isoprene, cyclooctene and cyclohexene. Operating at a pressure exceeding atmospheric pressure is useful if gaseous olefins are used, so as to allow them to be solubilised or liquefied under the reaction conditions. Operating at a temperature exceeding 0° C. has an effect on the reaction rate, although this is high even at temperature close to 0° C.

The manner of operating the process according to the present invention and its advantages will be more apparent from an examination of the following illustrative examples, which however are not limitative of the invention.

EXAMPLES 1–20

1.5 g of powdered catalyst, 45 cc of solvent and 1 mole of olefin are fed into a 250 cc glass autoclave (olefins which are gaseous at ambient temperature are fed with the autoclave sub-cooled). The autoclave is immersed into a bath temperature-controlled at the required temperature, and 0.3 to 0.6 moles of aqueous $H_2O_2$ (36% w/v) are fed by a metering pump over a period of 5–10 minutes, under magnetic agitation.

The residual $H_2O_2$ is checked periodically by withdrawing a solution sample and iodometrically titrating it. When it has practically disappeared, the autoclave is returned to ambient temperature, and the solution analysed by qualitative and quantitative gas chromatography.

The results obtained with various olefinic substrates and the relative reaction conditions are listed in Table 2.

The same epoxidation reactions can also be conducted in a fixed bed, as indicated in the following examples.

EXAMPLES 21–31

3.5 g of catalyst having a particle size distribution of 25–60 mesh are placed in a 6×4 mm steel tube 45 cm long and having a volume of 5 cc. A solution containing 200 ml of solvent and 20–40 g of olefin is prepared in a steel autoclave (in the cae of olefins which are gaseous at ambient temperature, the autoclave is pressurised at 15° C. with the same olefin until the required weight quantity has been attained). The tube containing the catalyst is immersed in a temperature-controlled bath, and pumping of the olefin solution is commenced simultaneously with the pumping of the aqueous $H_2O_2$ solution by means of two metering pumps, the throughputs being regulated so that the molar $H_2O_2$|olefin feed ratio is between 10 and 90%.

The operating pressure is regulated by means of a suitable valve at the catalytic reactor outlet to a pressure of between 1.5 and 15 ata and in any case greater than the pressure in the autoclave containing the olefin. The effluent is percolated through a condenser at 10° C. in order to condense all the condensable products, and is then collected and analysed by gas chromatography.

The results obtained are shown in Table 3.

EXAMPLES 32–34

To demonstrate that the $H_2O_2$ concentration has no effect on the epoxide-glycol distribution, Table 4 shows by way of example the results obtained with allyl chloride in methanol, under the operating conditions of Examples 1–20.

EXAMPLE 35

40 cc of isopropanol and 10 cc of water are fed into a 250 cc steel autoclave lined with teflon.

The autoclave is immersed in a bath temperature-controlled at 135° C., and pressurised to 35 ata with oxygen, the quantity absorbed being continuously made-up.

After an $O_2$ absorption of 0.2 moles (4.48 normal litres) the mixture is cooled, depressurised and the quantity of $H_2O_2$ and peroxides in the solution titrated. It contains 0.155 moles of peroxide oxygen (evaluated as $H_2O_2$).

40 cc of said solution are transferred to a glass autoclave together with 10 cc of $H_2O$ and 1 gram of titanium silicalite. 5 g of propylene are fed by sub-cooling the autoclave. The autoclave is then immersed under magnetic agitation into a bath temperature-controlled at 20° C. After 35 minutes the solution is analysed by gas chromatography and titrated to obtain the peroxide content. The following results are obtained:

| | |
|---|---|
| residual peroxides (as $H_2O_2$) | 5.5 mmoles |
| propylene oxide | 110 mmoles |
| propylene glycol | 8.5 mmoles |
| and thus: | |
| $H_2O_2$ conversion (peroxides) | = 95.56% |
| propylene oxide selectivity | = 92.83% |

TABLE 1

| TS – 1 | | | Silicalite[a] | | |
|---|---|---|---|---|---|
| $2\theta$ (Cu$k\alpha$) | Inter-planar distance d(Å) | Rel. Int.[b] | $2\theta$ (Cu$k\alpha$) | Inter-planar distance d(Å) | Rel. Int.[b] |
| 7.94 | 11.14 | vs | 7.94 | 11.14 | vs |
| 8.85 | 9.99 | s | 8.85 | 9.99 | s |
| 9.08 | 9.74 | m | 9.08 | 9.74 | m |
| 13.21 | 6.702 | w | 13.24 | 6.687 | w |
| 13.92 | 6.362 | mw | 13.95 | 6.348 | mw |
| 14.78 | 5.993 | mw | 14.78 | 5.993 | mw |
| 15.55 | 5.698 | w | 15.55 | 5.698 | w* |
| 15.90 | 5.574 | w | 15.90 | 5.574 | w |
| 17.65 | 5.025 | w | 17.65 | 5.025 | w |
| 17.81 | 4.980 | w | 17.83 | 4.975 | w |
| 20.37 | 4.360 | w | 20.39 | 4.355 | w |
| 20.85 | 4.260 | mw | 20.87 | 4.256 | mw |
| 23.07 | 3.855 | s | 23.08 | 3.853 | s |
| | | | 23.28 | 3.821 | ms |
| 23.29 | 3.819 | s | | | |
| | | | 23.37 | 3.806 | ms |
| | | | 23.71 | 3.753 | ms |
| 23.72 | 3.751 | s | | | |
| | | | 23.80 | 3.739 | ms |
| 23.92 | 3.720 | s | 23.94 | 3.717 | s |
| | | | 24.35 | 3.655 | mw |
| 24.41 | 3.646 | m | | | |
| | | | 24.60 | 3.619 | mw |
| | | | 25.84 | 3.448 | w |
| 25.87 | 3.444 | w | | | |
| | | | 25.97 | 3.431 | w |
| 26.87 | 3.318 | w* | 26.95 | 3.308 | w* |
| | | | 29.23 | 3.055 | w |
| 29.27 | 3.051 | mw | | | |
| | | | 29.45 | 3.033 | w |
| 29.90 | 2.988 | mw | 29.90 | 2.988 | mw |
| 30.34 | 2.946 | w | 30.25 | 2.954 | w |
| 45.00 | 2.014 | mw* | 45.05 | 2.012 | mw* |
| 45.49 | 1.994 | mw* | 45.60 | 1.989 | mw* |

[a]Prepared by the method of U.S. Pat. No. 4,061,724; product calcined at 550° C.
[b]vs: very strong; s: strong; ms: medium-strong; m: medium; mw: medium-weak; w: weak; *: multiplet.

TABLE 2

| N° | OLEFIN | SOLVENT | t(hours) | T° C. | F.R.* | $H_2O_2$ CONV. | EPOXIDE SELECT. | GLYCOL SELECT. | OTHERS | |
|---|---|---|---|---|---|---|---|---|---|---|
| 1 | ETHYLENE | CH$_3$OH | 0.5 | 0° C. | 50% | 99% | 85% | 5% | 10% | as glyme |
| 2 | ETHYLENE | ACETONE | 0.5 | 25° C. | 50% | 99% | 80% | 10% | 10% | as ketal |
| 3 | ETHYLENE | t-butyl alc. | 0.5 | 20° C. | 50% | 97% | 96% | 4% | | |
| 4 | PROPYLENE | CH$_3$OH | 0.5 | 0° C. | 58% | 100% | 86% | 5% | 9% | as ether |
| 5 | PROPYLENE | ACETONE | 0.5 | 40° C. | 40% | 97% | 80% | 10% | 10% | as ketal |
| 6 | PROPYLENE | t-butyl alc. | 0.8 | 40° C. | 50% | 90% | 96% | 4% | | |
| 7 | PROPYLENE | H$_2$O | 1 | 20° C. | 50% | 98% | 72% | 28% | | |
| 8 | ALLYL CHLORIDE | CH$_3$OH | 0.2 | 70° C. | 58% | 100% | 95% | 1% | 4% | as ether |
| 9 | ALLYL CHLORIDE | ACETONE | 0.5 | 70° C. | 50% | 97% | 95% | 1% | 3% | as ketal |
| 10 | BUTENE-2 | CH$_3$OH | 0.5 | 20° C. | 40% | 100% | 85% | 5% | 10% | as ether |
| 11 | BUTENE-2 | ACETONE | 0.8 | 40° C. | 50% | 98% | 82% | 10% | 8% | as ketal |
| 12 | BUTENE-2 | H$_2$O | 1 | 25° C. | 45% | 98% | 75% | 25% | | |
| 13 | OCTENE 1 | CH$_3$OH | 1 | 65° C. | 35% | 100% | 85% | 15% | 10% | as ether |
| 14 | OCTENE 1 | ACETONE | 1 | 60° C. | 35% | 100% | 85% | 10% | 5% | as ketal |
| 15 | OCTENE 1 | — | 2 | 75° C. | 30% | 100% | 83% | 17% | | |
| 16 | 1-TRIDECENE | ACETONE | 1.5 | 80° C. | 30% | 95% | 92% | 8% | | |
| 17 | MESITYL OXIDE | ACETONE | 1.5 | 80° C. | 25% | 97% | 94% | 6% | | |
| 18 | ISOPRENE | CH$_3$OH | 0.5 | 90° C. | 45% | 93% | 89% | 10% | 1% | |
| 19 | CYCLOOCTENE | ACETONE | 1.5 | 80° C. | 30% | 98% | 97% | 3% | | |
| 20 | CYCLOHEXENE | ACETONE | 1.5 | 75° C. | 35% | 99% | 98% | 2% | | |

*F.R. = feed ratio = $\dfrac{\text{moles } H_2O_2 \text{ fed}}{\text{moles olefins fed}}$

TABLE 3

| N° | OLEFIN. | SOLVENT. | T °C. | F.R. | PRODUCTIV. Kg/h × 1 | $H_2O_2$ CONVERS. | EPOXIDE SELECT. | GLYCOL SELECT. | OTHERS % | |
|---|---|---|---|---|---|---|---|---|---|---|
| 21 | ETHYLENE | CH$_3$OH | 10 | 45% | 3.02 | 99% | 88% | 3% | 9% | as glycol monomethylether |
| 22 | " | ACETONE | 10 | 50% | 2.00 | 92% | 91% | 5% | 4% | as glycol ketal |
| 23 | PROPYLENE | CH$_3$OH | 15 | 68% | 4.15 | 98% | 88.5% | 1.5% | 10% | as glycol monomethylether |
| 24 | " | ACETONE | 15 | 55% | 1.55 | 90% | 92% | 6% | 2% | as glycol ketal |
| 25 | " | t-butyl alc. | 20 | 55% | 2.20 | 85% | 96% | 4% | — | |

TABLE 3-continued

| N° | OLEFIN. | SOLVENT. | T °C. | F.R. | PRODUCTIV. Kg/h × 1 | H₂O₂ CONVERS. | EPOXIDE SELECT. | GLYCOL SELECT. | OTHERS % | |
|---|---|---|---|---|---|---|---|---|---|---|
| 26 | ALLYL Chloride | CH₃OH | 70 | 60% | 8.52 | 100% | 98% | 1% | 1% | as glycol mono ether |
| 27 | ALLYL Chloride | ACETONE | 70 | 60% | 4.53 | 92% | 98% | 2% | — | |
| 28 | BUTENE-2 | CH₃OH | 40 | 45% | 5.35 | 98% | 77% | 20% | 3% | as glycol monoether |
| 29 | " | ACETONE | 40 | 50% | 3.70 | 92% | 75% | 15% | 10% | as ketal |
| 30 | OCTENE-1 | ACETONE | 80 | 35% | 2.35 | 99% | 80% | 15% | 5% | as ketal |
| 31 | CYCLOHEXENE | CH₃OH | 80 | 40% | 2.12 | 99% | 83% | 7% | 10% | as glycol monomethylether |

TABLE 4

| N° | SOLVENT | H₂O₂ CONC. % w/v | F.R. | t(hours) | T °C. | EPOXIDE SEL. | GLYCOL SEL. | OTHERS |
|---|---|---|---|---|---|---|---|---|
| 32 | CH₃OH | 10% | 40% | 0.5 | 15° C. | 85.2% | 5.5% | 9.3% |
| 33 | " | 36% | 40% | 0.5 | 15° C. | 86.0% | 6.2% | 7.8% |
| 34 | " | 60% | 40% | 0.5 | 15° C. | 84.7% | 4.8% | 10.5% |

We claim:

1. A process for the expoxidation of olefinic compounds, characterised by reacting said compounds with hydrogen peroxide either introduced as such or produced by substances capable of generating it under the reaction conditions, in the presence of synthetic zeolites containing titanium atoms, of the following general formula:

$$xTiO_2 \cdot (1-x)SiO_2$$

where x lies between 0.0001 and 0.04, and possibly in the presence of one or more solvents.

2. A process as claimed in claim 1, characterised in that the epoxidation reaction is conducted at a temperature of between 0° and 150° C., and at a pressure of between 1 and 100 ata.

3. A process as claimed in claim 1, wherein the hydrogen peroxide is in dilute aqueous solution.

4. A process as claimed in claim 1, wherein the hydrogen peroxide in the aqueous solution is between 10 and 70% w/v.

5. A process as claimed in claim 1, wherein the solvent is polar.

6. A process as claimed in claim 5, wherein the polar solvent is chosen from alcohols, glycols, ketones, ethers and acids, having a number of carbon atoms less than or equal to 6.

7. A process as claimed in claim 6, wherein the alcohol is methanol or tert.butanol.

8. A process as claimed in claim 6, wherein the ketone is acetone.

9. A process as claimed in claim 6, wherein the acid is acetic acid or propionic acid.

10. A process as claimed in claim 1, wherein the olefinic compound is chosen from ethylene, propylene, allyl chloride, butene-2, 1-octene, 1-tridecene, mesityl oxide, isoprene, cyclooctene and cyclohexene.

11. A process for the epoxidation of olefinic compounds said process consisting essentially of the reaction of an olefin with 10-70% w/v aqueous hydrogen peroxide at a molar ratio of hydrogen peroxide to olefin of between 10 and 90% at a temperature of 0°-150° C. and a pressure of 1-100 atmosphere in the presence of a polar solvent and synthetic zeolites containing titanium atoms, of the general formula:

$$x\,TiO_2\,(1-x)\,SiO_2$$

wherein x lies between 0.0001 and 0.04.

12. A process as defined in claim 11, wherein the olefin is allyl chloride and the solvent methanol.

* * * * *